US005850019A

United States Patent [19]
Maiti et al.

[11] Patent Number: 5,850,019
[45] Date of Patent: Dec. 15, 1998

[54] PROMOTER (FLT) FOR THE FULL-LENGTH TRANSCRIPT OF PEANUT CHLOROTIC STREAK CAULIMOVIRUS (PCLSV) AND EXPRESSION OF CHIMERIC GENES IN PLANTS

[75] Inventors: Indu B. Maiti, Lexington, Ky.; Robert J. Shepperd, Portland, Oreg.

[73] Assignee: University of Kentucky Research Foundation, Lexington, Ky.

[21] Appl. No.: 692,511

[22] Filed: Aug. 6, 1996

[51] Int. Cl.$^6$ ............... A01H 5/00; A01H 5/10; C07H 21/04; C12N 1/21; C12N 5/14; C12N 15/82

[52] U.S. Cl. ............ 800/205; 435/172.3; 435/243; 435/252.8; 435/320.1; 435/419; 536/24.1; 800/250; 800/DIG. 9; 800/DIG. 13; 800/DIG. 14; 800/DIG. 17; 800/DIG. 24; 800/DIG. 26; 800/DIG. 27; 800/DIG. 42; 800/DIG. 43; 800/DIG. 44; 800/DIG. 56; 800/DIG. 57; 800/DIG. 58; 800/DIG. 63; 800/DIG. 65

[58] Field of Search ................. 536/24.1, 23.1, 536/23.2; 435/320.1, 410, 414, 419; 800/205, 250, DIG. 9, DIG. 13, DIG. 17, DIG. 24, DIG. 26, DIG. 27, DIG. 44, DIG. 42, DIG. 14, DIG. 43, DIG. 56, DIG. 57, DIG. 58, DIG. 65, DIG. 69, DIG. 63

[56] References Cited

U.S. PATENT DOCUMENTS

| | | |
|---|---|---|
| 5,188,642 | 2/1993 | Shah et al. . |
| 5,306,862 | 4/1994 | Chappell et al. . |
| 5,349,126 | 9/1994 | Chappell et al. . |
| 5,362,865 | 11/1994 | Austin . |
| 5,365,017 | 11/1994 | Chappell et al. . |
| 5,491,076 | 2/1996 | Carrington et al. . |
| 5,516,671 | 5/1996 | Lawrence et al. . |

FOREIGN PATENT DOCUMENTS

WO94/24848 11/1994 WIPO .

OTHER PUBLICATIONS

Indu B. Maiti et al., "Plants that express a potyvirus proteinase gene are resistant to virus infection", Proceedings of the National Academy of Sciences, Jul. 1, 1993, vol. 90, No. 13, pp. 6110–6114.

Indu B. Maiti et al., "Promoter/leader deletion analysis and plant expression vectors with the figwort mosaic virus (FMV) full length transcript (FLt) promoter containing single or double enhances domains", Transgenic Research 5, pp. 1–14, 1996.

G. Jason Smith et al., "Expression of Heterologous Genes Following Electroporation of the Marine Diatom Skeletonema Costatum", Plant Physiology, Abstract 803, Jun. 1995, vol. 108, No. 2.

Bird et al., "Transgenic Plants With Increased solids Content", Chemical Abstracts, vol. 119, Abstract No. 19725In, 1993, p. 260.

Franklin et al., "High Expression of a Foreign Gene in Transformed Bean Callus", In Vitro Cellular & Development Biology, Mar. 19, 1992, vol. 28, No. 2, Abstract p. 1119.

Rie Terada et al., "Expression of CaMV35S–GUS gene in transgenic rice plants", Molecular & General Genetics, vol. 220, pp. 389–392, 1990.

Ricky Yeargan et al., "Tissue partitioning of cadmium in transgenic tobacco seedlings and field grown plants expressing the mouse metallothionein 1 gene", Transgenic Research 1, 261–267 (1992).

Indu B. Maiti et al., "Properties of transgenic plants that express a functional potyirus P1 proteinase gene", 1995, pp. 1–18.

Indu B. Maiti et al., "Properties of transgenic plants that express a functional potyvirus p1 proteinase gene or a fused CP gene", 8th International Congress Molecular Plant–Microbe Interactions, Jul. 14–19, 1996, (Abstract #B–78).

Indu B. Maiti et al., "Expression of the Tobacco vein mottling irus nuclear inclusion protein (NIa) gene in tabacco", J. Cell. Biochem. Supplement 16F, (Abstract #Y213).

Indu B. Maiti et al., "Seed–Transmissable Expression of Mammalian Metallothionein in Transgenic Tobacco", Biochemical and Biophysical Research Communications, vol. 150, No. 2, 1988, pp. 640–647.

Indu B. Maiti et al., "Expression of the Tobacco Vein Mottling Virus Coat Protein (CP) and Cylindrical Inclusion Protein (C1) Gnes in Tobacco", 3rd International Contress Int. Soc. Plant Mol. Biol. meeting Oct. 6–11, 1991 (Abstract #1154).

Indu B. Maiti et al., "Plants that Express a Potyvirus Proteinase Gene are Resistant to irus Infection", proc. Natl. Acad. Sci., vol. 90, pp. 6110–6114 (1993).

Indu B. Maiti et al., "Light Inducible and Tissue–Specific Expression of a Chimeric Mouse Metallothionein cDNA Gene in Tobacco", Plant Science, 76 (1991) pp. 99–107.

Indu B. Maiti et al., "Inheritance and Expression of the Mouse Metallothionein Gene in Tobacco", Plant Physiol. (1989) 91, pp. 1020–1024.

Indu B. Maiti et al., "Deeloping Genetically Engineered Disease, Pest and herbicide Resistance in Tobacco", Recent Advances in Tobacco Science, vol. 18, Sep. 27–30, 1992, pp. 45–68.

Indu B. Maiti et al., "Multiple Potyvirus Genes do not confer Protection Upon Plants Additively", 4th Congress of ISPMB meeting, Jun. 19–24, 1994 (Abstract #1533).

Indu B. Maiti et al., "Promoter/leader deletion analysis and plant expressio vectors with the figwort mosaic virus (FMW) full lenth transcript (FLT) promoter containing single or double enhancer domains", Transgenic Research 6, 143–156 (1997).

(List continued on next page.)

*Primary Examiner*—Douglas W. Robinson
*Assistant Examiner*—Amy Nelson
*Attorney, Agent, or Firm*—McDermott, Will & Emery

[57] ABSTRACT

The isolation, modification and use of wild-type and modified viral FLt promoters of peanut chlorotic streak caulimovirus (PClSV) in the expression of chimeric genes in plant cells. The FLt promoter from PClSV has been modified to have duplicated enhancer domains.

**17

OTHER PUBLICATIONS

D.. Reddy et al., "Peanut Chlorotic Streak irus, a New Caulimoirus Infecting Peanuts (Arachis hypogaes) in India", The Amer. Phytopathological Soc., vol. 83, No. 2, 1993, pp. 129–133.

Richard Dean Richins, "Organizsation and Expression of the Peanut Chlorotic Streak Virus Genome", Abstract of Dissertation, 1993.

Indu B. Maiti et al., "Isolation and expression analysis of peanut chlorotic streak caulimoirus (PCISV) full length transcript (FLt) promoter in transgenic plants", Proceedings of Keystone Symposia, Apr. 6–11, 1997 (Abstract #214).

Chemical Abstract, vol. 122, Abstract No. 75400b, "Eukaryotic RNAse H shares a consered domain with caulimovirus proteins that facilitate translocation of polycistronic RNA", Arcady R. Musheigian et al., 1995.

Chemical Ahstract, vol. 118, Abstract No. 230014s, "The putatie zinc finger of a caulimovirus is essential for infectively but does not influence gene expression", Herman B. Scholthof et al., 1993.

Chemical Abstract, vol. 117, Abstract No. 186002q, "Regulation of caulimoirus gene expression and the involvement of cis–acting elements on both iral transcripts", Herman B. Scholthof et af Chemical Abstract, vol. 116, Abstract No. 249819p, "The ful–length transcript of a caulimovirus is a polycistronic mRNA whose genes are trans actiated by the product of gene VI", Herman B. Scholthof et al., 1992.

Chemical Abstract, vol. 116, Abstract No. 3719r, "A disease syndrome associated with expression of gene VI of caulimoviruses may be a nonhost reaction", Karen Beth Goldberg et al., 1992.

Chemical Abstract, vol. 116, Abstract No. 1417s, "The regions of sequence variation is caulimoirus gene VI", Margaret Sanger et al., 1992.

Chemical Abstract, vol. 106, Abstract No. 171526n, "Properties of ribonucleic acid and coat protein of peanut chlorotic ring mottle virus", Fumiyoshi Fukumoto et al., 1987.

Chemical Abstract, vol. 123, Abstract No. 307774c, "Gene I mutants of peanut chlorotic streak irus, a caulimoirus, replicate in plants but do not moe from cell to cell", D.A. Ducasse et al., 1995.

Chemical Abstract, vol. 122, Abstract No. 235454c, "A defective movement protein of TMV in transgenic plants confers resistance to multiple viruses whereas the functional analog increases susceptibility", Bret Cooper et al., 1995.

Chemical Abstract, vol. 118, Abstract No. 251150y, "Peanut chlorotic streak virus, a new caulimovirus infecting peanuts (*Arachis hypogaea*) in India", D.V.R. Reddy et al., 1993.

Chemical Abstract, vol. 118, Abstract No. 120793n, "Gene I of peanut chlorotic streak virus, a caulimovirus; is it involved in virus movement?", Daniel Ducasse et al., 1993.

Chemical Abstract, vol. 122, Abstract No. 232376t, "Molecular analysis of the essential and nonessential genetic elements in the genome of peanut chlorotic streak caulimovirus", A.R. Mushegian et al., 1995.

Symposium Abstract No. 214, "Isolation and expression analysis of peanut chlorotic streak caulimovirus (PCISV) full length trascript (FLt) promoter in transgenic plants.— Metabolic Engineering in Transgenic Plants", Keystone Symposia Sponsored by The Samuel Roberts Noble Foundation, Inc. in Copper Mountain, Colorado, Apr. 6–11, 1997.

Koziel MG, et al. "Optimizing expression of transgenes with an emphasis on post–transcriptional events." Plant Mol. Biol. 32: 393–405 1996.

```
                              SEQ ID NO:1
                 3b
ACAGAGGGATTTCTCTGAAGATCATGTTTGCCAGCTATGCGAACAATCAT        -230(5848)

5b
CGGGAGATCTTGAGCCAATCAAAGAGGAGTGATGTAGACCTAAAGCAATA        -180(5898)

6b        4b         6a         5a        4a
ATGGAGCCATGACGTAAGGGCTTACGCCATTACGAAATAATTAAAGGCTG        -130(5948)

3a                       2b
ATGTGACCTGTCGGTCTCTCAGAACCTTTACTTTTTATATTTGGCGTGTA         -80(5998)

2a             1b    1a
TTTTTAAATTTCCACGGCAATGACGATGTGACCTGTGCATCCGCTTTGCC         -30(6048)
                                   +1
TATAAATAAGTTTTAGTTTGTATTGATCGACACGATCGAGAAGACACGGC         +21(6098)

CATTTGGACGATCATTTGAGAGTCTAAAAGAACGAGTCTTGTAATATGTT         +71(6148)

(Construct # 114-GUS)
pKLP6GUS
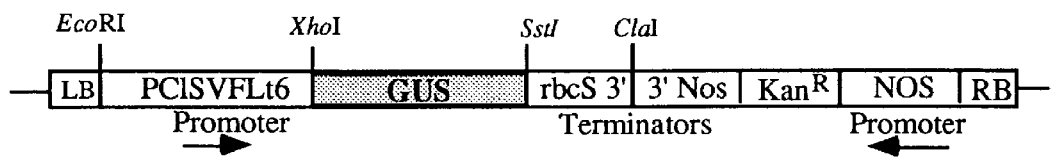
(Construct # 116-GUS)
pKLP36GUS
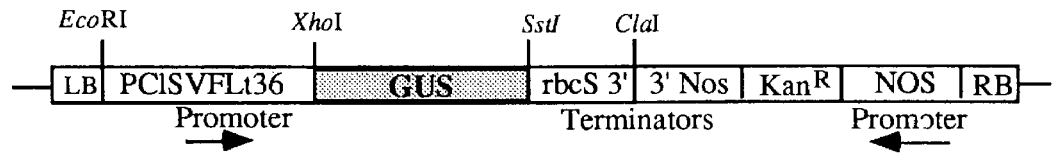
FIG. 6

PROMOTER (FLT) FOR THE FULL-LENGTH TRANSCRIPT OF PEANUT CHLOROTIC STREAK CAULIMOVIRUS (PCLSV) AND EXPRESSION OF CHIMERIC GENES IN PLANTS

TECHNICAL FIELD

The present invention relates to the fields of plant genetic engineering and plant molecular biology. More particularly, the present invention relates to the isolation, modification and use of wild-type and modified viral FLt promoters of peanut chlorotic streak caulimovirus (PClSV) in the expression of chimeric genes in plant cells. The FLt promoter from PClSV has been identified by the present inventors and modified to have duplicated enhancer domains.

The FLt promoter with its single or double enhancer domains when linked to heterologous coding sequences to form chimeric gene constructs showed high levels of expression of these genes in cells and transgenic plants. These chimeric genes have been shown to be well expressed in plant cells. The FLt promoter with its double enhancer domain gives better expression of genes compared to the FLt promoter with its single enhancer domain in transformed plants. However, both plasmids with enhancer domains show improved levels of expression over promoters without enhancer domains. This invention also includes plant cells, plant tissue, and differentiated plants and seeds under control of the FLt promoter of PClSV.

The invention is particularly directed to plasmids such as pPCSV22CAT containing the full-length transcript promoter of the peanut chlorotic streak caulimovirus. The plasmid is used to express chimeric genes in plants.

BACKGROUND ART

A virus is a group of submicroscopic infective agents with double or single stranded DNA or RNA as core genetic material surrounded by a protein (and lipid in some cases) shell called a 'capsid' or 'coat'. It has no semipermeable membrane and it can multiply only in living cells using host cellular components. The short segment of the virus genetic material (FLt promoter) used in this invention can not infect plants or other organisms to cause disease. It is useful with selected foreign genes to obtain expression of these genes in other plants to confer useful properties to those transgenic plants.

The caulimoviruses and their promoters

The following is a description of caulimoviruses also called plant pararetroviruses. Caulimoviruses derived their name from cauliflower mosaic virus (CaMV), the type member of the group (for reviews see Shepherd, 1989; Covey and Hull, 1992). More than a dozen types of caulimoviruses have been described to date. All have small circular DNA molecules as their genetic material. The genomes of CaMV (Gardner, et al., 1981) and four other members of this group, namely carnation etched ring virus (CERV), (Hull, et al., 1986), figwort mosaic virus (FMV), (Richins, et al.,1987) soybean chlorotic mottle virus (SOCMV), (Hasegawa, 1989), and peanut chlorotic streak virus (PClSV) (Richins, 1993) have been fully sequenced. CaMV is a circular double stranded DNA virus with a genome size of approximately 8 kb. It is organized into seven open reading frames (genes) and two intergenic regions. In the case of CaMV and by analogy PClSV, the polypeptides corresponding to the six genes (I to VI) have been detected in infected cells and their functions have been identified. The cell-to-cell movement function (Thomas, et al., 1993; Ducasse et al., 1995), aphid-transmission factor (Daubert et al., 1983; Woolson, et al., 1983), minor capsid protein (Giband, et al., 1986), major capsid protein (Daubert, et al., 1982), reverse transcriptase (Takatsui, et al., 1992), and post-transcriptional transactivator (Bonneville et al., 1989) (also the inclusion body protein, Odell and Howell, 1980) are associated with ORFs I to VI respectively.

Gene VII protein was not detected in vivo (Wurch, et al., 1991); and its function is not clearly established. However a sequence located with this ORF of FMV is involved in translation of viral genes (Gowda, et al., 1991). The viral genome is replicated through reverse transcription of the terminally redundant full-length transcript (Bonneville and Hohn, 1993) by a virus encoded reverse transcriptase. Two major viral transcripts, known as 35S RNA and 19S RNA are synthesized exclusively from the minus strand DNA by the host RNA polymerase II (Odell, et al., 1981; Howell and Hull, 1978).

The large intergenic region (L-IR) which resides between gene VI and VII, contains the promoter (35S) for the full-length transcript which spans the entire viral genome (Dixon and Hohn, 1984; Scholthof, et al., 1992). The 35S RNA serves as template for minus strand DNA synthesis by viral gene V encoded reverse transcriptase (Gordon, et al., 1988). The small intergenic region (S-IR) residing between gene V and gene VI contains a promoter (19S) which transcribes gene VI only (Odell and Howell, 1980). The PClSV is apparently lacking the S-IR sequence, however both FMV (Scholthof, et al., 1992) and PClSV (Richins, 1993) have also been shown to have transcripts similar to the 19S and 35S RNA found in CaMV infected plant cells.

Regulatory elements of the cauliflower mosaic virus 35S promoter

The CaMV 35S promoter, which spans about 941 base pair (bp) upstream from the transcription start site, has been shown to be active in various monocot and dicot cells. The cis-regulatory elements that are involved in directing transcription initiation reside within this region. The CaMV 35S promoter has a modular construction with elements consisting of an enhancer (Lam, 1994, and references there in) similar to those of other promoters like that of SV40 in mammalian systems (Ondek, et al., 1987; Schirm, et al., 1987; Fromental, et al., 1988). The 5' deletion analysis of CaMV35S promoter, studied in transformed tobacco calli or a protoplasts transient assay system, indicates that a promoter fragment of 343 bp upstream from the transcription start site is sufficient for high promoter activity (Odell, et al., 1985, Ow, et al., 1987).

The high promoter activity is the result of synergistic and combinatorial effects of enhancer elements residing in the −343 to −46 region upstream of the TATA element promoter (−46 to +8) (Fang, et al., 1989, Benfey, et al., 1989, Benfey and Chua, 1990, Benfey, et al., 1990a and Benfey et al., 1990b).

Sequence motifs and Trans-acting factors in the CaMV promoter

Several protein binding sequence motifs have been identified in the enhancer region of the 35S promoter (Lam, et al., 1989; Lam and Chua, 1989; Prat, et al., 1989; Bouchez, et al., 1989, Yanagisawa and Izui, 1992). Identical or similar sequence motifs are also present in promoters of other caulimoviruses (Bouchez, et al., 1989; Sanger, et al., 1990; Cooke and Penon, 1990; Richins, et al., 1993). Two nuclear binding protein factors, known as Activating Sequence Factor-1 and -2 (ASF-1 and ASF-2) from tobacco have been well characterized. ASF-1 binds to the activating sequence as-1 (−82 to −62) region of 35S promoter. Two TGACG motifs within this site are essential for DNA-protein interaction (Lam, et al., 1989). The as-1 motif is also found in full-length transcript promoters from other caulimovirus including FMV (Sanger, et al., 1990, and present studies), PClSV (Richins, 1993) and MMV (Shepherd group, unpublished observation).

Modification of Promoter with multiple copies of an enhancer domain

Single or multiple copies of enhancer sequences from the CaMV 35S promoter can increase homo- and heterologous promoter activity in an orientation-independent manner (Kay, et al., 1987; Ow, et al., 1987: Odell, et al., 1988; Fang, et al., 1989; Driesen, et al., 1993; Omirulleh, et al., 1993). The enhancement of promoter activity was proportional to the copy number of the enhancer sequence (Kay, et al., 1987; Ow, et al., 1987; Omirulleh, et al., 1993). Similar observation was made when single or multiple copies of the enhancer sequence was inserted upstream of the TATA element of the CaMV19S promoter (Ow, et al., 1987; Driesen, et al., 1993), rbcS-3A promoter (Fang, et al., 1989), the nos promoter (Odel, et al., 1988) or the FMV FLt promoter (Maiti, et al.,1995,1996)

The engineering of novel traits in plants and other crops promises to be an area of great agricultural importance (Maiti and Hunt, 1992; Wagner, 1992). Plant genetic engineering techniques allow researchers to introduce heterologous genes of interest into plant cells to obtain the desired qualities in the plants of choice. Plant genetic engineering is leading to rapid progress in the production of economically valuable germplasm with improved characters or traits such as insect resistance, virus resistance, fungal resistance, herbicide resistance, bacterial or nematode pathogen resistance, cold or drought tolerance, improved nutritional value, seed oil modification, delayed ripening of fruits, and male sterility, to name a few. These germplasms provide enhanced developments in breeding programs for crops improvement as well as a better understanding of gene regulation and organization in transgenic plants. The expression of useful new traits in plants is a major focus in plant biotechnology.

Plant metabolic engineering is the application of genetic engineering methods to modify the nature of chemical metabolites in plants. For metabolic engineering where multiple genes need to be inserted into one cell, the use of different strong constitutive promoters is desirable in order to avoid genetic instability caused by recombination between identical or closely related promoter sequences, for example those taken from plants themselves. Through use of these promoter sequences the introduced genes can be transcribed to messenger RNA and then translated to resultant proteins to exhibit new traits or characters.

Besides developing useful traits in crops, transgenic plants lead to a further understanding of molecular pathways involved in disease development and secondary metabolism in plants. Moreover, by engineering plants with specific foreign genes, the responses of plants to abiotic and biotic stress and stress-related metabolism are analyzed. The invention described herein which develops gene vectors with newly defined promoters of the caulimoviruses advances this effort.

A wide variety of well-characterized genes of animal, human, bacterial and of plant origin, including those of several viruses, are available for engineering plants. For the most effective expression of this wide selection of genes either constitutive or regulated, versatile gene expression vectors are required. At the University of Kentucky, Dr. Arthur Hunt and his colleagues have developed a series of plant expression vectors (Schardl, at al., 1987) with a constitutive 35S promoter from cauliflower mosaic virus (CaMV) which have been successfully used to produce transgenic plants (Maiti, et al., 1988, 1989, 1991, 1993, 1994, 1995; Graybosh, et al., 1989; Berger, et al., 1989; Yeargan, et al., 1992; Liod, et al., 1992).

The most widely used promoter for plant transformation, as described earlier, has been the 35S promoter of CaMV. It is active in a wide variety of plants and tissues. It also is the most thoroughly characterized promoter with respect to the sequence elements active in its transcriptional activity (Benfey and Chua, 1990. Kay, et al., 1987 showed that the transcriptional activity of the CaMV 35S promoter could be increased approximately tenfold by making a tandem duplication of 250 base pairs of upstream sequence. Similar observations have been made with other promoters (McNeall, et al., 1989). A similar construct has been tested with the FMV—and FLt promoters.

Certain promoters have a specific modular sequence which makes them either tissue-specific, developmentally regulated or environmentally regulated for the selective expression of genes in cells. Promoters capable of directing RNA synthesis at higher rates compared to other promoters are desirable for many purposes. If these promoters are able to direct the expression of genes in most types of plant tissues, they are defined as constitutive promoters. Previous work had established that the CaMV 35S promoter is one of the strongest constitutive promoters. The transcriptional activity of the CaMV 35S promoter is the result of synergistic and combinatorial effects of enhancer elements residing upstream of the TATA element. Single or multiple copies of the enhancer sequences from the CaMV 35S promoter can also increase the activity of heterologous promoters in an orientation—independent manner. The enhancement of promoter activity has been found to be related to the copy number of the enhancer sequence. We have developed expression vectors with the PClSV promoter with its single and duplicated enhancer domains. The upstream enhancer elements of the strong constitutive promoter from the full-length transcript of FMV or PClSV has been doubled in a strategy to strengthen this promoter even further.

Promoters from other caulimoviruses such as FMV, and MMV, as well as the better characterized CaMV 35S promoter are found to be useful for plant genetic engineering. The Monsanto Co. has recently patented the 35S and the 19S promoters of CaMV in USA, and the full-length transcript promoter from FMV in Europe. The inventors have now developed new promoters of equal or better strength.

U.S. Pat. No. 5,306,862 to Chappell, et al., discloses a method and composition for increasing sterol accumulation in higher plants. Column 8, lines 44–46 discloses the cauliflower mosaic virus promoter 35S.

U.S. Pat. No. 5,349,126 to Chappell et al., discloses a process and composition for increasing squalene and sterol accumulation in higher plants. Column 4, lines 20–24 describe the cauliflower mosaic virus 35S promoter. The patent describes the pKYLX71 recombinant plasmid.

Chemical Abstracts, Volume 118, Abstract No. 120793n, 1993, discloses the gene I of peanut chlorotic streak virus.

Chemical Abstracts, Volume 118, Abstract No. 251150y, 1993, discloses a physical map of the peanut chlorotic streak virus which is transmissible in plants of Leguminosae and Solanaceae. The virus was determined not to be related to the cauliflower mosaic virus and the figwort mosaic virus. Polypeptides were purified of the peanut chlorotic streak virus having 58 and 51 kDa. The virus is found to have a 8.1 kilo base pair length.

Chemical Abstracts, Volume 122, Abstract No. 232376t, 1995, discloses a molecular analysis of the essential and nonessential genetic elements of the peanut chlorotic streak caulimovirus.

Chemical Abstracts, Volume 122, Abstract No. 235454c, 1995, discloses reduced accumulation of tobacco mosaic virus in upper of leaves and plants inoculated with the peanut chlorotic streak caulimovirus.

Chemical Abstracts, Volume 123, Abstract No. 307774c, 1995, discloses gene I mutants of peanut chlorotic streak virus. Gene I is suspected of encoding a protein for virus movement.

Chemical Abstracts, Volume 106, Abstract No. 171526yn, 1987, discloses properties of ribonucleic acid in coat protein of the peanut chlorotic ring model virus.

Chemical Abstracts, Vol. 116, Abstract No. 1417s, 1992 discloses the regions of sequence variation in caulimovirus gene VI. The figwort mosaic virus is used as a comparison.

Chemical Abstracts, Vol. 116, Abstract No. 3719r, 1992 discusses the disease syndrome associated with expression of gene VI and caulimoviruses. There is a correlation between the level of gene VI and coded protein found in the disease.

Chemical Abstracts, Vol. 116, Abstract No. 249819p, 1992 discloses the full-length transcript of the caulimovirus as a polycistronic messenger RNA whose genes are transactivated by the product of gene VI. The results show that the genome of figwort mosaic virus contains two promoters.

Chemical Abstracts, Vol. 117, Abstract No. 186002q, 1992 discloses regulation of caulimovirus gene expression and involvement of cis-acting elements on viral transcripts.

Chemical Abstracts, Vol. 118, Abstract No. 230014s, 1993 discloses that a zinc finger of a caulimovirus is essential for infectivity but does not influence gene expression.

Chemical Abstracts, Vol. 122, Abstract No. 75400b, 1995, discloses that eukaryotic RNAse H shares a conserved domain with caulimovirus protein.

Chemical Abstracts, Vol. 122, Abstract No. 232376t, 1995 discloses a molecular analysis of essential and non-essential genetic elements in the peanut chlorotic streak caulimovirus.

Chemical Abstracts, Vol. 123, Abstract No. 251578x, 1995 discloses regulatory elements involved in caulimoviral gene expression.

Plant expression vectors with the constitutive FLt promoter from PClSV have been developed by the present inventors.

The present inventors have overcome deficiencies in prior art concerning transgenic plant promoters, and have developed useful promoters from PClSV for high level expression of foreign genes, for example, in transgenic tobacco. These vectors are be useful for both direct DNA uptake by isolated protoplasts and Ti plasmid-mediated gene transfer. Enhanced levels of transcription via highly active promoters are essential for high levels of gene expression in transgenic plants.

SUMMARY OF THE INVENTION

These inventions are in general applicable to plant genetic engineering. Specifically, the present inventions relate to the promoters from peanut chlorotic streak virus (PClSV) and these promoters direct the expression of genes in plant cells. A conventional gene is composed of a promoter region, a sequence encoding a 5' non-translated leader sequence of the transcribed messenger RNA, the structural gene itself and a 3' polyadenylation sequence. The promoter is a DNA fragment composed of modular sequence which directs and regulates the transcription to messenger RNA, the first step in expression of a gene.

The proper regulatory signals/enhancer elements should be present in a defined location in order to express the inserted gene first as RNA and then as a resultant protein via the process of translation. The 3'-polyadenylation sequence is a non-translated region which signals the adenylation of the 3' end of the RNA in order to stabilize the RNA in the cytoplasm for subsequent translation into protein.

An objective of the present invention is to define and document the strong constitutive FLt promoter of PClSV to be used for expression of chimeric genes in transgenic plants. An additional object is to describe a strategy to further strengthen the promoter from the full-length transcript of other members of the caulimoviruses including PClSV.

Thus the present invention provides a plasmid comprising a chimeric gene comprising a full-length transcript (FLt) promoter from peanut chlorotic streak virus (PClSV) operably linked to at least one heterologous gene sequence which is heterologous to the promoter.

The invention also provides for plant cells and transgenic plants which contain the plasmid of the invention.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIG. 1 shows the DNA sequence of the full-length transcript promoter from peanut chlorotic caulimovirus (PClSV; Richins, et al., 1993). The nucleotide sequence (PClSV coordinates 5799 to 6150, a 352 bp fragment) includes the 3' end of gene VI (SEQ ID NO:1), and part of the large intergenic region, presented from left to right in the 5' to 3' direction of the transcript.

FIG. 6 shows a schematic representation of chimeric GUS constructs used for assaying PClSVFLt promoter expression activity in transgenic plants.

STATEMENT OF DEPOSIT

Figure 2A:
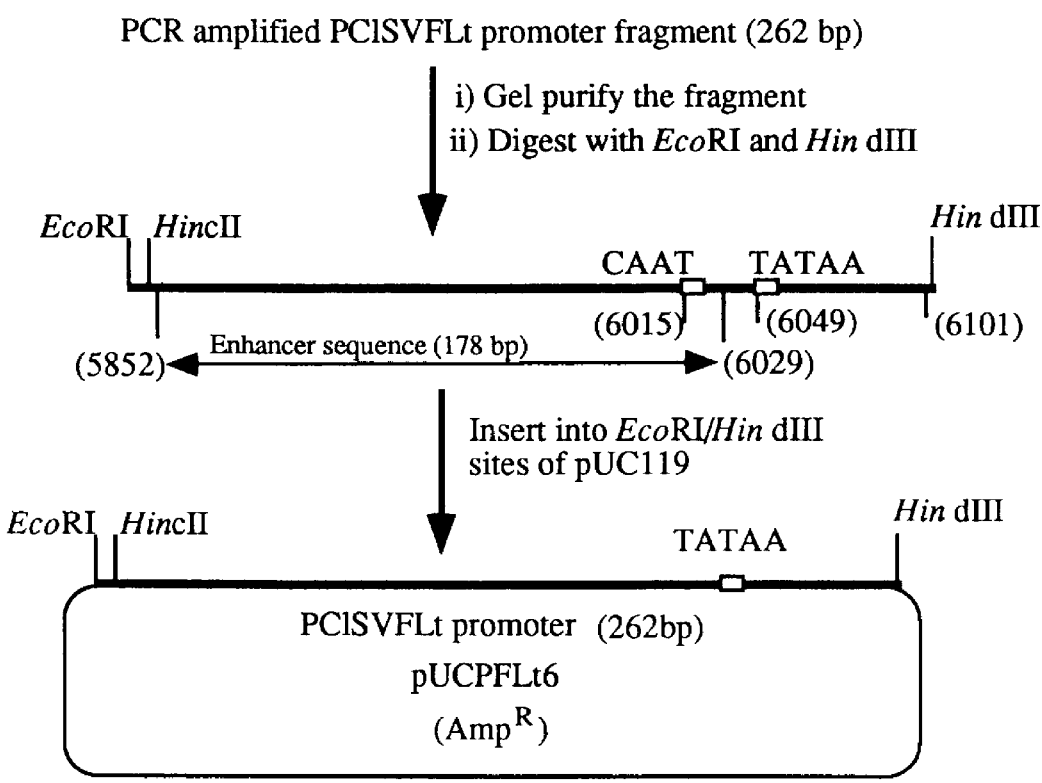
FIGS. 2A and 2B show the construction strategy of PClSV FLt promoter with single and double enhancer domains.

Plasmids pKLP6 and pKLP36 in *E. coli* TB1 have been deposited with the Agricultural Research Service (ARS) Patent Culture Collection (NRRL), 1815 North University Street, Peoria, Ill., USA, 61604, under the terms of the Budapest Treaty on Jul. 25, 1996. The deposit will be maintained for the life of the patent as required by Treaty.

DETAILED DESCRIPTION OF THE INVENTION

The invention provides for a plasmid or transformation vector comprising a chimeric gene comprising a full-length transcript (FLt) promoter from peanut chlorotic streak virus (PClSV) operably linked to at least one heterologous gene sequence which is heterologous to the promoter. In a preferred embodiment the plasmid further comprises at least one PClSV enhancer domain. The plasmid may include a single or double enhancer domain.

In an alternative embodiment of the plasmid, the promoter directs transcription of heterologous genes downstream from said promoter, in plants. The promoter preferably comprises nucleotides 5799 to 6150 of the 3' portion of gene VI (SEQ ID NO:1) and a downstream intergenic region of the PClSV genome. The promoter may also comprise a 5' non-translated leader sequence from peanut chlorotic streak virus.

In a more preferred embodiment of the invention the plasmid further comprises a region of homology to an *Agrobacterium tumefaciens* vector and a T-DNA border region from *Agrobacterium tumefaciens*, wherein said chimeric gene is located between the T-DNA border and the region of homology. Similarly this embodiment of the invention may possess at least one PClSV enhancer domain. The expression vector may further comprise a disarmed plant tumor-inducing plasmid of *Agrobacterium tumefaciens*.

Preferred plasmids in accordance with the invention are plasmids selected from PKLP6, PKLP36 and PCSV22CAT. Methods for obtaining these plasmids and characteristics of these plasmids are described herein. For example, a plasmid of the invention may comprise, in the 5' to 3' direction, a) the PClSV FLt promoter with single enhancer; b) a 3' nontranslated polyadenylation sequence of rbcS E9 gene; and (c) a structural sequence encoding neomycin phosphotransferase II.

The invention provides for a plant cell which comprises the plasmid of the invention. The plant cell may express the plasmid with at least one PClSV enhancer domain.

More importantly, the invention provides for transgenic plants which express the plasmid of the invention. In a preferred embodiment the transgenic plant is selected from, but not limited to cotton, soy bean, alfalfa, oilseed rape, flax, tomato, sugar beet, sunflower, potato, tobacco, maize, wheat, rice, lettuce and banana plants. The transgenic plant may express a heterologous gene present in the plasmid of the invention in plant tissue selected from, but not limited to calyx, filament, pedicel, style, ovary, corolla, anther, stigma, embryo, seeds, leaf, stem and root tissues.

In sum, the invention includes any DNA construct comprising a PClSV promoter, and preferably includes a PClSV FLt promoter isolated from a PClSV protein-encoding DNA sequence. The DNA construct may be expressed in plant cells. The DNA construct is transcribed and translated in plant cells, and includes promoters such as a PClSV FLt promoter region free of PClSV protein-encoding DNA sequence and a PClSV FLt promoter region with a DNA sequence which is heterologous with respect to the promoter. In a preferred embodiment the construct comprises a DNA sequence which is heterologous with respect to the promoter and a 3' non-translated polyadenylation signal sequence.

Thus, the present invention includes the following: i) isolation of the promoter for the full-length transcript (FLt) of peanut chlorotic streak virus from a full-length viral DNA clone (Reddy, et al., 1993) as described below in Experimental Section. ii) The invention provides for modification of the PClSV promoter to include duplication or multimerization of the enhancer domain of the Flt promoter from PClSV. The FLt promoter sequence for PClSV is shown in FIG. 1. iii) The invention provides for use of PClSV promoter in a method for transforming plant cells, expression vectors including PClSV promoter, a chimeric gene including PClSV promoter sequence, and transgenic plants, plant cells and seeds incorporating the PClSV promoter in a chimeric gene.

Experimental Procedures

Peanut chlorotic streak virus (PClSV) is a newly described member of the caulimovirus group (Reddy, et al., 1993). It has been partially characterized in this laboratory (Richins et al., 1993; Reddy, et al., 1993) These investigations provide the materials (DNA clones) for the invention described herein.

EXAMPLE 1

Construction of PClSV FLt promoter with its single and double enhancer elements and creation of plasmids pKLP6 and pKLP36

The construction strategy for isolating the PClSV FLt promoter and its enhancer is shown in FIGS. 2 A and B. The basic FLt promoter of PClSV, 150 bp (position 5852 to 6001 of the PClSV sequence) (SEQ ID NO:2) was isolated after amplification by PCR using oligonucleotides containing the appropriate sites to generate EcoRI-HincII sites at the 5' end and a HindIII site at the 3' end of the fragment. The promoter sequence was inserted as an EcoRI-HindIII fragment into the corresponding sites of the plant expression vector pKYLX71 (FIG. 3) and the plasmid pUC119. The resulting plasmids were designated pKLP6 (FIG. 4) and pUCPFLt6, respectively (FIG. 2A). The upstream sequence containing enhancer elements, a 78 bp (position 5852 to 5929) (SEQ ID NO:3) of the PClSV FLt promoter was amplified by PCR with oligonucleotides engineered for the EcoRI-HincII sites at the 5' end and the SmaI-HindIII sites at the 3' end of the fragment.

Figure 2B:
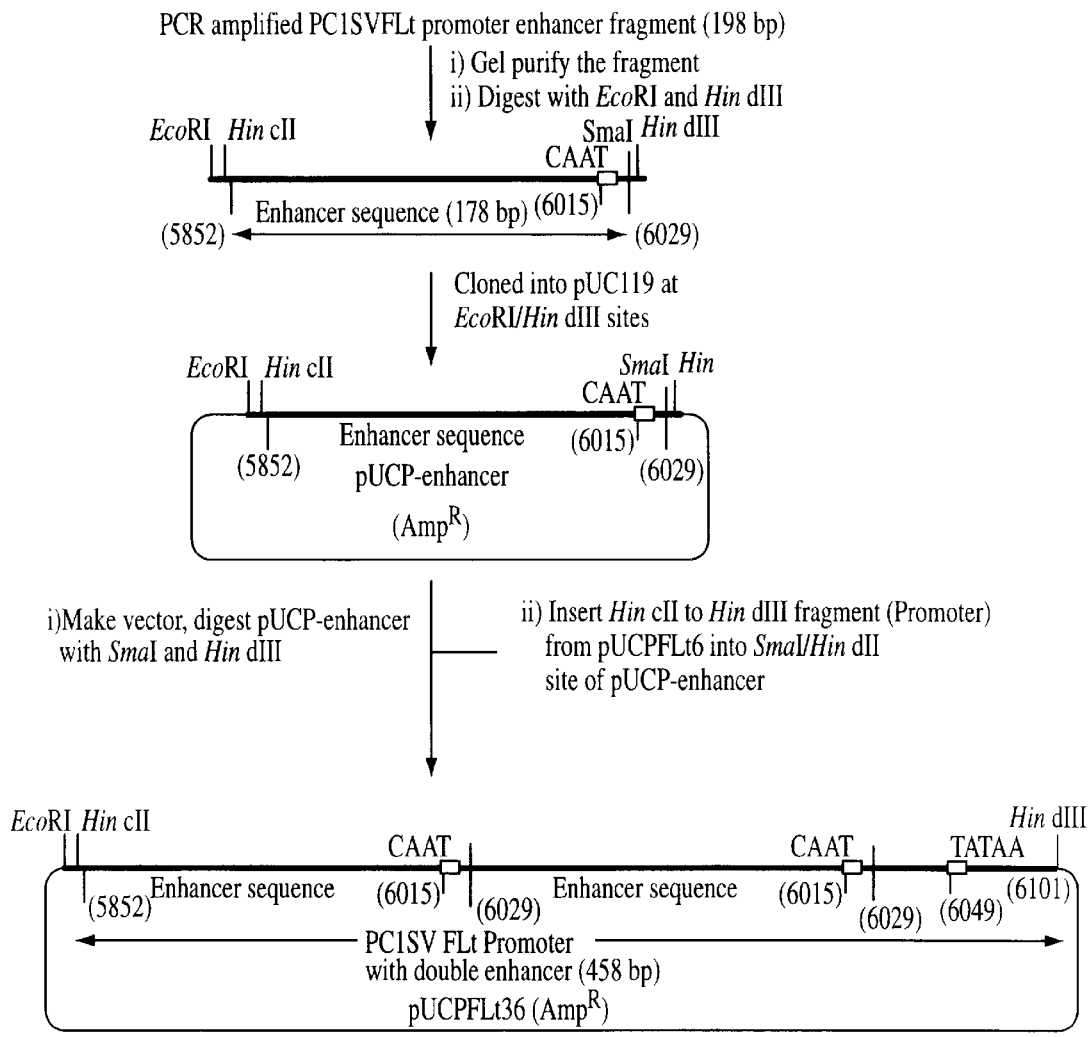
Figure 3:
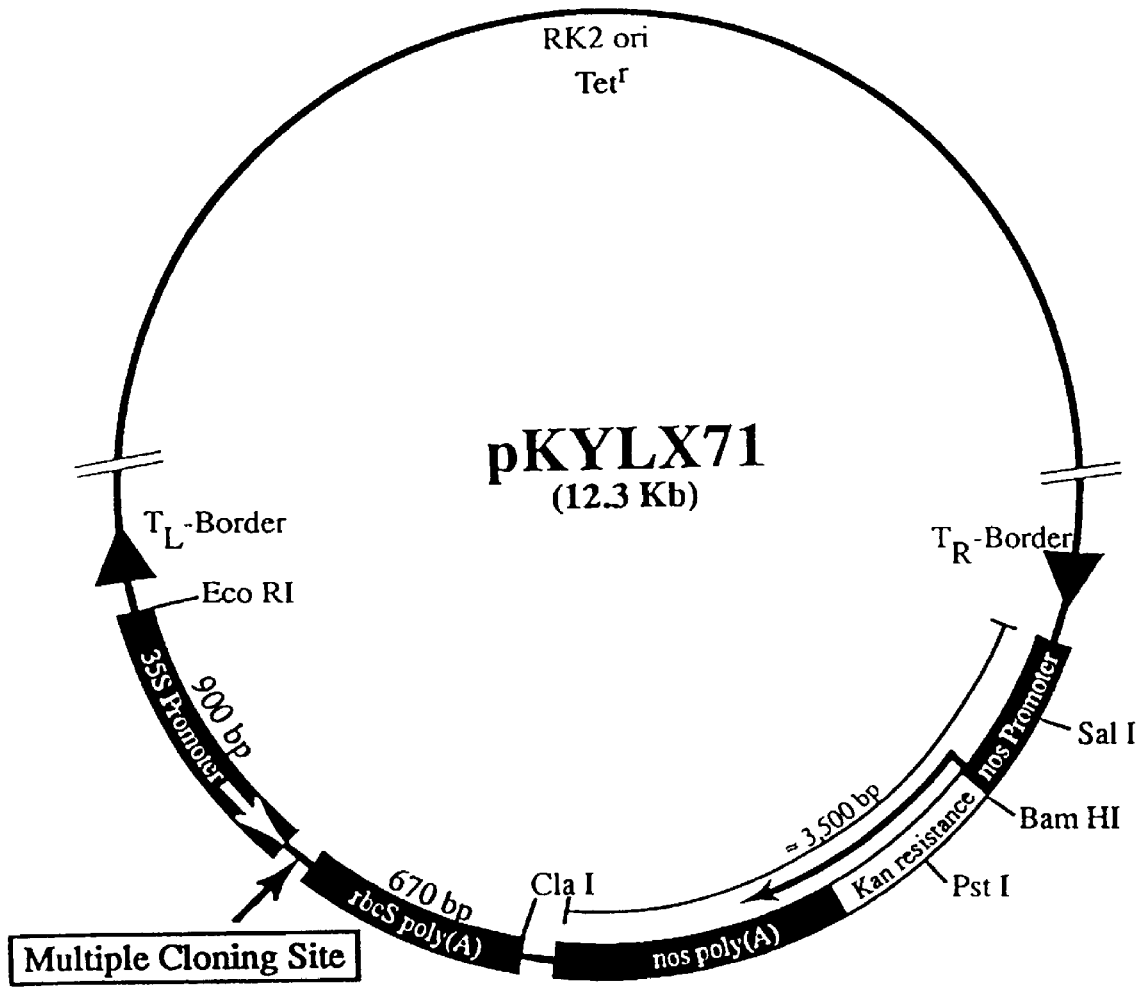
FIG. 3 shows a physical map of pKYLX71.
Figure 5:
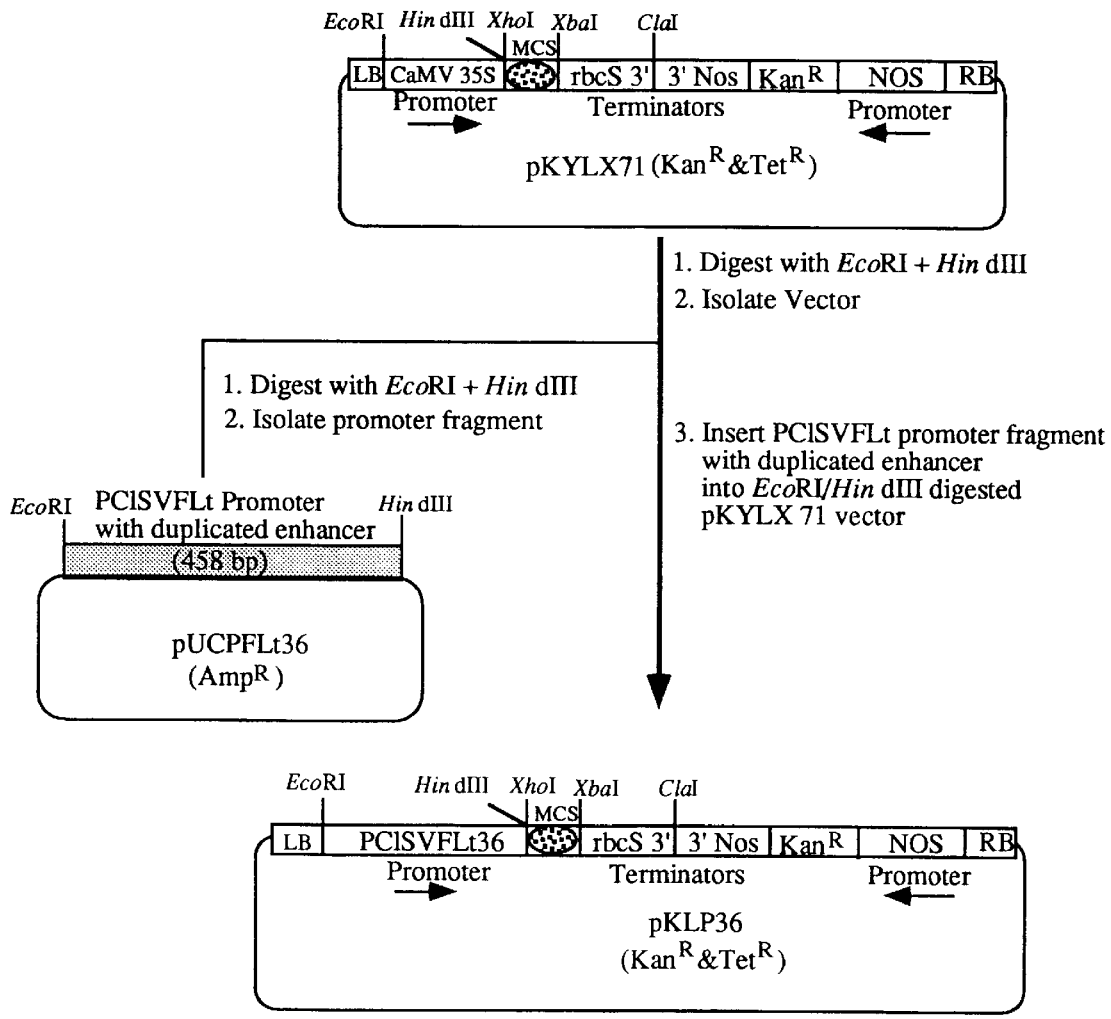
FIG. 5 shows a physical map of pKLP36.

The enhancer element fragment was cloned into EcoRI and HindIII sites of PUC119 and the plasmid designated as pUCP-enhancer (FIG. 2B). The PClSV FLt basic promoter fragment as a HincII-HindIII fragment (isolated from pUCPFLt6) was inserted into the pUCP-enhancer plasmid after digestion with SmaI and HindIII. The resulting plasmid designated as pUCPFLt36 contains two copies of the enhancer elements (FIG. 2B). The PClSVFLt promoter with its double enhancer domain was inserted into the plant expression vector pKYLX71 at its unique EcoRI and HindIII sites that flank the promoter. The resulting plasmid was designated as pKLP36 (FIG. 5). The PClSV basic FLt promoter and enhancer elements was amplified from a full-length clone of PClSV (Reddy et al., 1993).

EXAMPLE 2

Testing the Expression Vectors with a GUS reporter gene Stable transformation and analysis of transgenic plants.

The reporter gene GUS was tailored by PCR to include just the coding sequence with the initiation and termination codons, flanked by a Xho I site at the 5' end and a Sst I site at the 3' end. The PCR isolated fragment for the reporter gene (GUS) was digested with Xho I and Sst I, gel purified and cloned into the corresponding sites of the plant expression vectors PKLP6 and pKLP36 and the resulting constructs pKLP6GUS and pKLP36GUS were introduced into *Agrobacterium tumefaciens* strain C58C1:pGV3850 by triparental mating. Tobacco (cv. Samsun NN) was transformed with the engineered Agrobacterium as described earlier (Maiti et al., 1993). To examine the integration of genes in transgenic plants, genomic DNA was isolated following the procedure (Thomson and Henry, 1993) for PCR analysis.

The integration of reporter GUS gene in the genome of transgenic plants (R0 and R1 progeny) was detected by PCR amplification using appropriately designed oligonucleotides specific for the GUS gene sequence. Specificity of each PCR product was tested by Southern hybridization with a GUS probe. Although the GUS gene was used in this example as the gene heterologous to the PClSV promoter, any gene heterologous to the PClSV promoter which is desired to be expressed in a transgenic plant may be included in the plasmid. One of skill in the art can readily substitute any heterologous gene into the plasmid of the invention using conventional genetic engineering techniques.

Examples Heterologous Genes which may be used with PClSV FLt Promoter

Plant genetic engineering techniques allow researchers to introduce heterologous genes of interest into plant cells to obtain the desired qualities. A strong constitutive promoter like PClSV promoter is useful to direct the any gene to be used for plant genetic engineering, a field of biotechnology which is leading a rapid progress in the production of economically valuable germplasm with improved characters or traits such as:

1. Insect resistance, (developed with Bt toxin gene, α-amylase inhibitor gene).
2. Virus resistance, (developed with CP, protease or replicase gene).
3. Fungal resistance, (developed with chitinase gene, ribosome inhibiting protein gene, glucanase gene).
4. Herbicide resistance, (developed with acetolactate synthase, phosophinothricin acetyl transferase or bar gene, nitrilase gene, or 2,4-dichlorophenoxyacetate monooxygenase gene).
5. Bacterial or nematode pathogen resistance, (developed with α-hordothionin gene, Bt toxin gene, beet cyst nematode resistant locus).
6. Cold or drought tolerance.
7. Improved nutritional value, (developed with seed storage protein genes).
8. Seed oil modification, (developed by controlling chain length and saturation with fatty acid synthesis genes including stearoyl-ACP desaturase, oleoyl-ACP thioesterase, β-ketoacyl-ACP synthase and acyl-ACP thioesterase).
9. Delayed ripening of fruits, (developed by controlling ethylene producing genes, ACC oxidase gene).
10. Male sterility.
11. Modification of carbohydrate (developed with antisence gene of granule bound starch synthase, branching enzyme encoding genes, glgB).
12. Protein/peptides controlling human disease (Therapeutic peptides, proteins such as RMP-7, AC137, antithrombin hirudin, growth hormone, interleukin could be produced in plant-based system) to name a few examples.

The above heterologous genes, and other heterologous genes may be inserted into plasmids pKLP6 and pKLP36 by genetic engineering methods known in the art. These newly created germplasms can enhance breeding programs for crop improvement, as well providing as a better understanding of gene regulation and organization in transgenic plants. Plant metabolic engineering is the application of genetic engineering methods to modify the nature of chemical metabolites in plants. For metabolic engineering where multiple genes need to be inserted into one cell, the use of different, strong, constitutive promoters is desirable in order to avoid genetic instability caused by recombination between identical or closely related promoter sequences taken from plants themselves. Through use of the promoter sequences of the invention the introduced genes can be transcribed to messenger RNA and then RNA translated to resultant proteins that exhibit new traits or characters. The invention described herein, in developing gene vectors with newly defined promoters of the caulimoviruses, advances this effort.

A wide variety of well-characterized genes of animal, human, bacterial and of plant origin, including those of several viruses, are available for engineering plants. For the most effective expression of this wide selection of genes either constitutive or regulated, versatile gene expression vectors are required.

EXAMPLE 3

Comparative functional analysis of the CaMV35S and the FMV FLt promoters in transient expression experiments using tobacco leaf protoplasts:

In earlier studies (Maiti, et al., 1996) the relative strengths of the CaMV 35S and the FMV FLt promoters were compared. Different vector constructs with the GUS gene in transient expression experiments in protoplasts of *Nicotiana edwardisonii* were tested. Later the expression of the FMV FLt promoter with the PClSV FLt promoter in transgenic plants was compared (see example 2).

Isolation of protoplasts from *Nicotiana edwardsonii* cell suspension cultures and electroporation of protoplasts with supercoiled plasmid DNA containing GUS has been described (Gowda et al., 1989; Kiernan et al., 1993). Fluorometric GUS assays to measure GUS activity of plant tissue extracts and histochemical GUS assays to determine the distribution of GUS activity in plants, embryos and seedlings, were performed according to published procedures (Jefferson et al. ,1987). Protein in plant extracts was estimated (Bradford 1976) using BSA as a standard. The fluorometric GUS assays was performed as described earlier (Maiti et al., 1996).

The results from the transient expression experiments are shown in Table 1. The gene constructs with the wild-type FLt promoter (pFMV 20 GUS) with its single enhancer domain showed about 2.5 fold higher promoter activity than the CaMV 35S promoter-GUS construct (pGG1) in these assays. A control plasmid pc-GUS (CaMV 35S promoter-GUS-nos 3' terminator) contains an extra out of frame ATG codon (as Sph I site GCATGC) in the multiple cloning site of pKYLX 7. The presence of this ATG codon causes about 7–8 fold less GUS activity compared to pGG1. The duplication of FMV FLt promoter enhancer domain in plasmid pKLF2-GUS increased the level of GUS activity about 4 fold as compared to pKLF-GUS with the single enhancer domain. This difference was also observed in a stably transformed system in intact tobacco plants (Maiti, et al., 1996).

EXAMPLE 4

Comparative functional analysis of FMV and PClSV FLt promoters in transgenic plants The constructs shown in FIG. 6 were introduced into tobacco plants via the Agrobacterium co-cultivation method as described earlier (Maiti et al., 1988). Transformations were done using *Nicotiana tabacum* cv Samsun NN. Primary transformants of tobacco were selected for resistance to kanamycin (300 mg/ml) and these were grown to maturity in the greenhouse. At least 8–10 independent lines were generated for each construct tested. The expression levels of the GUS reporter gene in independent transformants developed for pKLP6GUS, pKLP36GUS are shown in FIG. 7. The expression from the PClSV FLt promoter was compared with that from the FMV promoter.

Individual plant lines generated from independent calli expressing the same gene showed variable GUS activity. Similar patterns of plant-to-plant variations in gene expression have been reported with many other plant promoters as pointed out earlier (Maiti et al., 1996). Most of the plant lines developed with pKLF36GUS showed more activity than any of the plants transformed with pKLP6GUS. On average, about 3 fold higher activity was exhibited by plants transformed with pKLP36GUS, which has a duplicated enhancer domain as compared to plants transformed with pKLP6GUS which has a single enhancer domain. Hence, the PClSV FLt promoter with a duplicated enhancer domain is more active than the FLt promoter with a single enhancer domain. These constitutive promoters developed from PClSV and FMV FLt promoter were comparable in respect to expression of reporter genes in transgenic plants.

EXAMPLE 5

Expression levels in seedlings (R1 progeny) and young tobacco plants

In order to examine the promoter activity in various tissues during seedling development, the expression of the GUS reporter gene in seedlings (R1 progeny) transformed with pKLP6GUS, or pKLP36GUS was examined by flurometric assay of tissue extracts and by histochemical staining of transverse sections of leaves, stems and roots. The PClSV promoter activity was monitored in 15 day old seedlings grown aseptically on an MS-agar medium in the presence of kanamycin (300 µg/ml) and 3% sucrose. Several independent lines for each construct were studied.

Comparison of activities of the FLt promoter indicated a gradient of expression in the following order; the highest level of activity was found in roots followed by leaves and stems. The histochemical staining shown in FIG. 8 is representative of the staining patterns analyzed in plants expressing high levels of GUS activity. In seedlings and sections of young leaves stained for GUS, the intensity of staining was markedly greater in vascular tissues of young leaves, petioles, stems and roots.

The intensity of GUS staining observed in vascular tissue was in the following order: roots>leaves>stems (FIG. 8). The histochemical GUS assay in leaves showed more activity in midribs, veins and other vascular tissue, and in trichomes, than in leaf mesophyll and palisade cells (data not shown). No GUS activity was detected in transgenic plants containing the construct pKLP36CAT gene (FIG. 8A).

The disarmed Agrobacterium strain transformed with plant expression vectors containing chimeric genes of interest can be used to engineer plants including but not limited to cotton, soybean, alfalfa, oilseed rape, flax, tomoto, sugar beet, sunflower, potato, tobacco, maize, wheat, rice and lettuce, banana. The use of DNA fragments or vectors including the PClSV promoter sequence tailored with heterologous DNA sequence in the transformation of plants by electroporation or particle gun transformation is within the scope of this invention. These embodiments and examples are provided in order to evaluate the practice of the present invention. These examples serve mainly illustrative purposes, and are not intended to limit the scope of the invention.

TABLE 1

| Constructs | Relative GUS activity (%) |
|---|---|
| Control (TE buffer) | 00 |
| pUC8 GUS (No promoter) | 00 |
| pc-GUS (extra ATG) | 7 |
| PGG1 (CaMV35S) | 35 |
| pFMV 20-GUS (FMV FLt) | 100 |
| pKLF (FMV FLt modified) | 100 |
| pKLF 2 (2 × Enh FMV FLt) | 410 |

Table 1: Relative β-glucuronidase (GUS) activity of GUS fusion constructs containing different promoters electroporated into tobacco protoplasts. The GUS assay was carried out 20 hrs after electroporation. Assays and conditions were as described in the Methods. Promoter strength is presented as percentage of GUS activity normalized to pFMV 20 GUS for pUC based constructs or pKLFGUS for pKYLX7 based constructs, and represent the mean of three samples from at least two independent experiments, variation was within 12% of the presented value.

Figure 7:
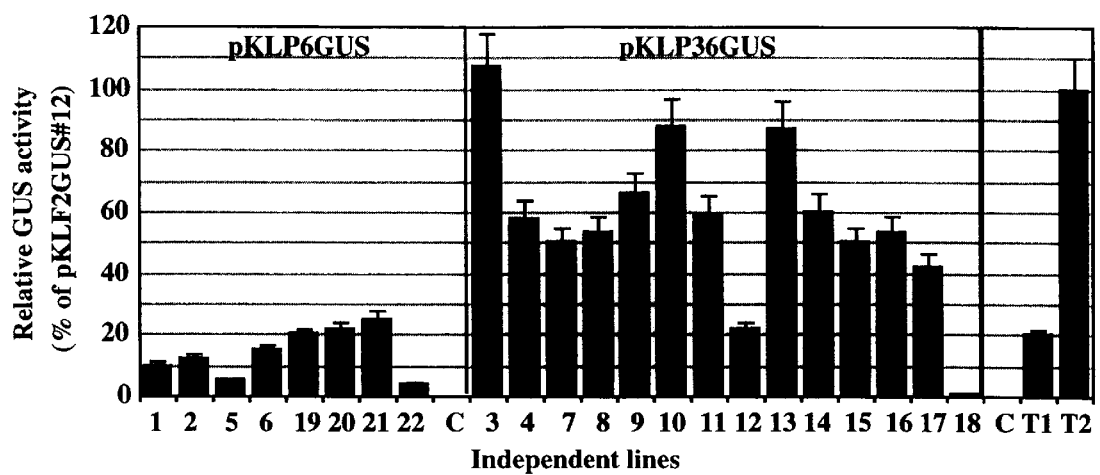
FIG. 7 shows a PClSV FLt promoter activity in transgenic plants expressing a GUS reporter gene.
Figure 8A:
FIG. 8 shows histochemical localization of GUS activity in developing transgenic tobacco plants.
Figure 8B:
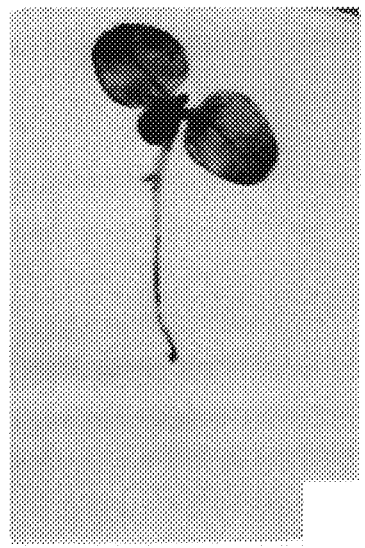
Figure 8C:
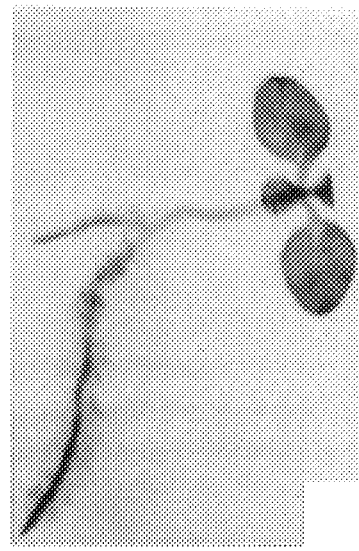
Figure 8D:
Figure 8E:
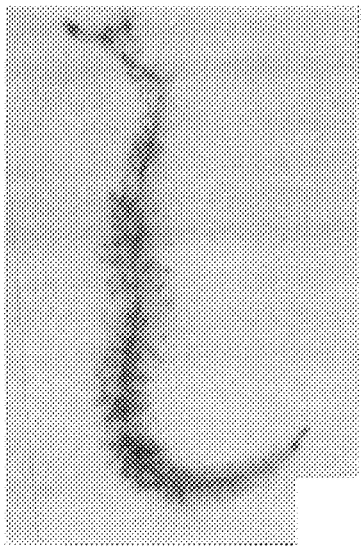
Figure 8F:
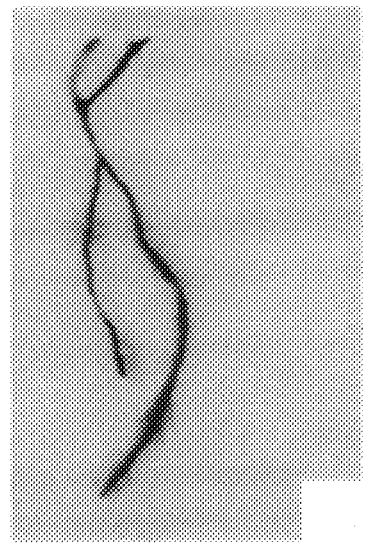

FIG. 7 shows a comparison of the FMV promoter with the PClSV. These results suggest that expression of the FMV and PClSV are comparable and that the PClSV promoter is stronger than the CaMV promoter.

DETAILED DESCRIPTION OF THE FIGURES

FIG. 1. The DNA sequence of the full-length transcript promoter from the peanut chlorotic caulimovirus, (PClSV), (Richins et al., 1993). The nucleotide sequence (PClSV coordinates 5799 to 6150, a 352 bp fragment) includes the 3' end of gene VI (SEQ ID NO:1), and part of the large intergenic region, presented from left to right in the 5' to 3' direction of the transcript. The TATA box, CCACT box are shown in bold. The transcription initiation site for the full-length FMV transcript is indicated as +1, (position 6078). Repeat sequence domains (1a, 1b; to 6a, 6b as indicated) are under lined or overlined. These sequence motif may be important for the promoter function.

FIGS. 2A and 2B show a construction strategy of PClSV FLt promoter with its single and double enhancer domains. Number in parenthesis indicate nucleotide position in PClSV genome. MCS, multiple cloning sites FIG. 3. Physical map of pKYLX71.

Figure 4:
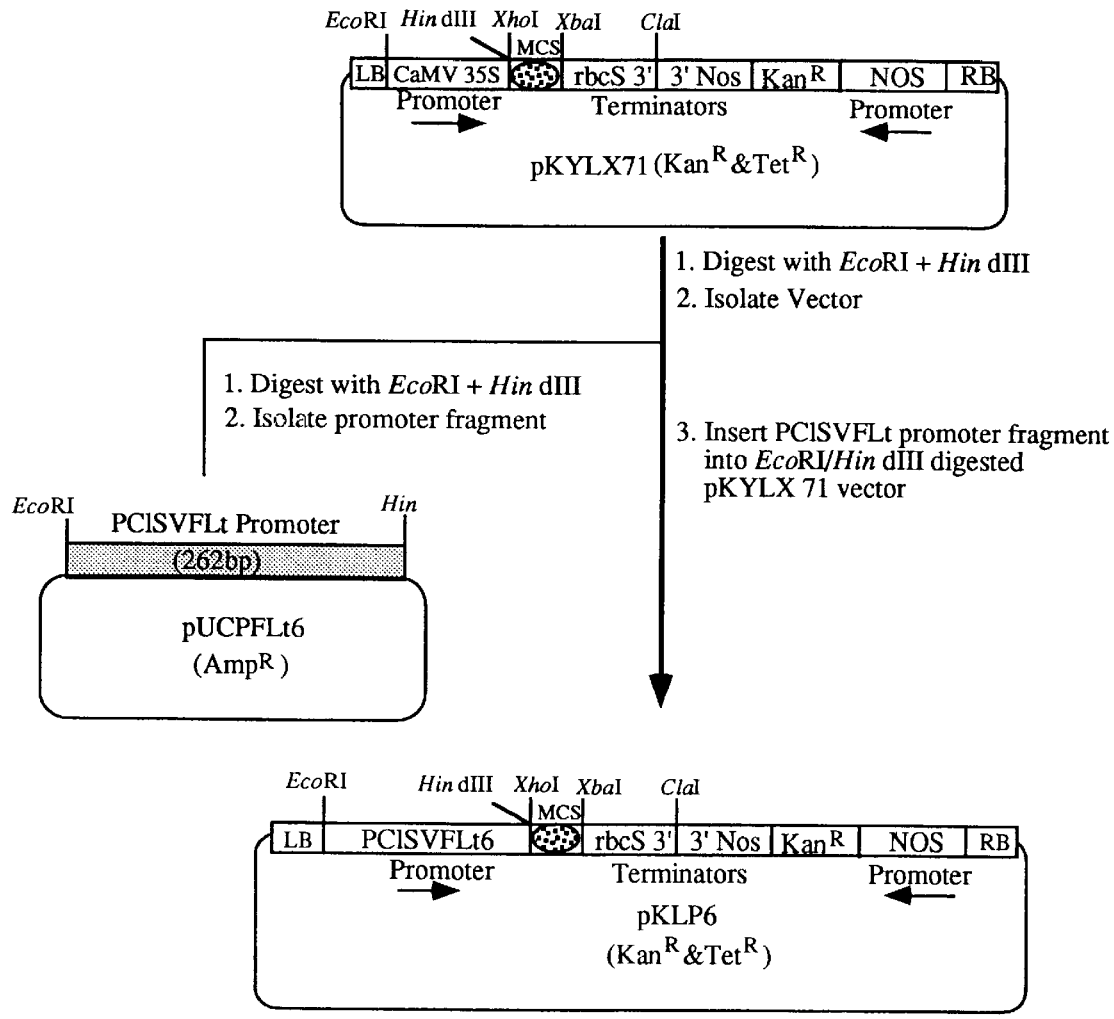
FIG. 4 shows a physical map of pKLP6.

FIG. 4. Physical map of pKLP6; MCS, multiple cloning sites.

FIG. 5. Physical map of pKLP36; MCS, multiple cloning sites FIG. 6. Schematic representation of chimeric GUS constructs used for assaying PClSVFLt promoter expression activity in transgenic plants. The identity of the respective promoter is shown for each plasmid. GUS represents the gene for β-glucuronidase of E. coli. The position of restriction sites XhoI,SacI, EcoRI, HindIII ClaI used to assemble these plasmids are shown. The position of the left and right T-DNA borders (LB and RB respectively) the rbcS polyadenylation signal (3' REGION) and the Kmr gene are illustrated. NT3' or RT3' represent the polyadenylation sequences from NOS or RbcS gene respectively.

FIG. 7. PClSV FLt promoter activity in transgenic plants expressing GUS reporter gene. Comparative analysis of the PClSV FLt promoter activity in independent transgenic plants *Nicotiana tabacum* cv Samsun NN (2 week old seedlings, R1 progeny/second generation) expressing a GUS reporter gene. Independent transgenic lines were developed with PClSV FLt promoter in construct pKLP6GUS containing a single enhancer domain, and in construct pKLP36GUS containing a double enhancer domains. Seeds obtained from transgenic plants were germinated in presence of kanamycin (200 μg/ml). GUS activity was determined in tissue extracts from whole seedlings. Independent plants were developed for constructs pKLP6GUS line # 1, 2, 5, 6, 19, 20, 21, and 22; and for construct pKLP36 line # 3, 4, 7, 8, 9, 10, 11, 12, 13, 14, 15, 16, 17 and 18. (C) Negative control, tissue extract from Samsun NN (wt). Positive control, one of the best expressing lines either from (T1) pKLF GUS line #11 with FMV FLt promoter with single enhancer domain or (T2) pKLF2GUS line #12 with double enhancer domain compared with PClSV FLt promoter. GUS activity are presented as % activity of the best expressing pKLF2GUS#12 line with FMV FLt double enhancer domain. The presented data is the mean of three samples from at least two independent experiments, variation was within 10% of the presented value.

FIG. 8. Histochemical localization of GUS activity in developing transgenic tobacco.

A. Transgenic tobacco seedlings (X4), (pKLP36CAT, R1 progeny) with CAT gene, no GUS activity was detected.

B. Seedling (X4), (pKLP6 GUS #21, R1 progeny) 14DAI; GUS activity was localized in root and leaves.

C. Seedling (X4), (pKLP36 GUS #3, R1 progeny) 14DAI; GUS activity was localized in roots, roots hairs and leaves.

D. Roots (3X) from six week old plants pKLP36CAT, R1 progeny, no GUS activity was detected.

E. Roots (3X) from six week old plants pKLP6GUS #21, R1 progeny, GUS activity was detected in roots.

F. Roots (X3) from six week old plants pKLP36GUS #3, R1 progeny, GUS activity was detected in roots.

REFERENCES

An, G., Costa, M. A., Mitra, A., Ha, S-B. and Marton, L. (1988) Organ-specific and developmental regulation of the nopaline synthase promoter in transgenic tobacco plants. Plant Physiol. 88: 547–552.

Benfey, P. N, Ren, L. and Chua N-H (1990a) Tissue-specific expression from CaMV 35S enhancer subdomains in early stages of plant development. EMBO J. 9: 1677–1684.

Benfey, P. N. and Chua, N-H. (1990). The cauliflower mosaic virus 35S promoter: Combinatorial regulation of transcription in plants. Science 250: 959–966.

Benfey, P. N., Ren, L and Chua, N-H. (1990b) Combinatorial and synergistic properties of CaMV 35S enhancer subdomains. EMBO J. 9: 1685–1696.

Benfey, P. N., Ren, L. and Chua, N-H. (1989) The CaMV 35S enhancer contain at least two domains which can confer different developmental and tissue-specific expression patterns. EMBO J. 8: 2195–2202.

Berger, P. H., Hunt, A. G., Domier, L. L., Hellmann, G. M. Stram, Y., Thornbury, D. W. and Pirone, T. P. Expression in transgenic plants of a viral gene product that mediates insect transmission of potyviruses. Proc. Natl, Acad. Sci. (USA) 86: 8402–8406.

Bonneville, J. M., Sanfacon, H., Futterer, J. T., Hohn, T. (1989). Posttranscriptional trans-activation in cauliflower mosaic virus. Cell 59: 1135–1143.

Bonneville, J. M. and Hohn, T. (1993) In "Reverse Transcriptase" (A. M. Skalka and S. P. Goff, eds), pp357–390, Cold Spring Harbor Laboratory Press, Cold Spring Harbor, N.Y.

Bouchez, D., Tokuhisa, J. G., Llewellyn, D. J., Dennis, E. S. and Ellis, J. G. (1989) The ocs-element is a component of the promoters of several T-DNA and plant viral genes. EMBO J. 8: 4197–4204.

Bradford, M. M. (1976) A rapid and sensitive method for the quantitation of microgram quantities of protein utilizing the principle of protein-dye binding. Anal. Biochem. 72: 248–254.

Cooke, R. and Penon, P. (1990). In vitro transcription from cauliflower mosaic virus promoters by a cell-free extract from tobacco cells. Plant Mol. Biol. 14: 391–405.

Covey, S. N. and Hull. R. (1992) Genetic engineering with double-stranded DNA viruses. In: "Genetic engineering with plant viruses" (T. M. A. Wilson and J. W. Davis, eds), pp 217–249. CRC Press, Boca Ratonl, Fla.

Daubert, S., Richins, R. D., Shepherd, R. J., and Gardner, R. C. (1982) Maping of the coat protein gene of cauliflower mosaic virus by its expression in a prokaryotic system. Virology 122: 444–449.

Daubert, S., Shepherd, R. J., and Gardner, R. C. (1983) Insertional mutagenesis of the cauliflower mosaic virus genome. Gene 25: 201–208.

Ducasse, D. A. Mushegian, A. R. and Shepherd, R. J. 1995. Gene I mutants of peanut chlorotic streak virus, a caulimovirus replicate in planta but do not move from cell to cell. Jour. Virology 69: 5781–5786

Dixon, L. and Hohn, T. (1984) Initiation of translation of the cauliflower mosaic virus genome from a polycistronic mRNA evidence from deletion mutagenesis. EMBO J. 3: 2731–2736.

Driesen, M., Benito-Moreno, R-M., Hohn, T., and Futterer, J. (1993) Transcription from the CaMV 19S promoter and autocatalysis of translation from CaMV RNA. Virology 195: 203–210.

Fang, R-X., Nagy, F., Sivasubramanian, S. and Chua, N-H. (1989) Multiple cis regulatory elements for maximal expression of the cauliflower mosaic virus 35S promoter in transgenic plants. Plant Cell 1: 141–150.

Fromental, C., Kanno, M., Nomiyama, H. and Chambon, P. (1988) Cooperativity and hierarchical levels of functional organization in the SV 40 enhancer. Cell 54: 943–953.

Gardner, R. C., Howarth, A. J., Hahn, P., Brown-Leudi, M. and Shepherd, R. J (1981) The complete nucleotide sequence of an infectious clone of cauliflower mosaic virus by M13mp7 shortgun sequencing. Nucleic Acids Res. 9: 2871–2888.

Giband, M., Mesnard, J-M., and Lebeurier, G. (1986). The gene III product (P15) of cauliflower mosaic virus is a DNA—binding protein while an immunologically related P11 polypeptide is associated with virions. EMBO J. 5: 2433–2438.

Gordon, K., Pfeiffer, P., Futterer, J. and Hohn, T. (1988) In vitro expression of cauliflower mosaic virus genes. EMBO J. 7: 309–317.

Gorman, C. M., Moffat, L. F. and Howard, B. H. (1982) Recombinant genomes which express chloramphenicol acetyltransferase in mammalian cells. Mol. Cell Biol. 2: 1044–1051.

Gowda, S., Scholthof, H. B., Wu, F. C. and Shepherd, R. J. (1991) Requirement of gene VII in cis for the expression of downstream genes on the major transcript of figwort mosaic virus. Virology 185: 867–871.

Gowda, S., Wu, F. C., Herman, H. B. and Shepherd, R. J. (1989) Gene VI of figwort mosaic virus (caulimovirus group) functions in posttranscriptional expression of genes on the full-length RNA transcript. Proc. Natl. Acad. Sci. USA 86: 9203–9207.

Graybosh, R., Hellmann, G. M., Shaw, J. G., Rhoads, R. E. and Hunt, A. G. 1989. Expression of a potyvirus nonstructural protein in transgenic tobacco. Biochem. Biophys. Res. Commun. 160: 425–432.

Hasegawa, A., Verver, J., Shimada, A., Saito, M., Goldbach, R., van Kammen, A., Miki, K., Kameya-Iwaki, M. and Hibi, T. (1989) The complete sequence of soybean chlorotic mottle virus DNA and the identification of a novel promoter. Nucl. Acids Res.17: 9993–10013.

Howell, S. H. and Hull, R. (1978) Replication of cauliflower mosaic virus and transcription of its genome in turnip leaf protoplasts. Virology 86: 468–481.

Hull, R., Sadler, J. and Longstaff, M. (1986) The sequence of carnation etched ring viral DNA: comparison with cauliflower mosaic virus and retroviruses. EMBO J. 5: 3083–3090.

Jefferson, R. A., Kavanagh, T. A. and Bevan, M. W. (1987) GUS fusion: β-Glucuronidase as a sensitive and versatile gene fusion marker in higher plants. EMBO J. 6: 3901–3907.

Kay, R., Chan, R., Daly, M. and McPherson, J. (1987) Duplication of CaMV 35S promoter sequence creats a strong enhancer for plant genes. Science 236: 1299–1302.

Kiernan, J. M., Wu, F. C., Goldberg, K-B., Gowda, S. and Shepherd, R. J. (1993) Transformation in *Nicotiana edwardsonii*, In: Biotechnology in Agriculture and Forestry, Vol 22, Plant Protoplasts and Genetic Engineering III, (Ed Y.P.S. Bajaj), Springer-Verlag Berlin Heidelberg.

Lam, E. (1994) Analysis of tissue-specific elements in the CaMV 35S promoter. In: Results and Problems in Cell differentiation, Vol 20, 181–196, L. Nover (ed, Plant Promoters and transcription factors, Springer-Verlag Berlin Heidelberg.

Lam, E., Benfey, P. N., Gilmartin, P. M., Fang, R-X. and Chua, N-H. (1989) Site-specific mutation alter in vitro factor binding and change promoter expression pattern in transgenic plants. Proc. Natl. Acad. Sci. USA 86: 7890–7894.

Lam, E. and Chua, N-H. (1989) GT-1 binding site confers light responsive expression in transgenic tobacco. Science 248: 471–474.

Liod, A. M., Walbot, V., Davis, R. W. (1992) Arabidopsis and *Nicotiana anthrocyanin* production activated by maize regulators R and C1. Science 258: 1773–1775.

Maiti, I. B., Gowda, S., Kiernan, J., Ghosh, S. K., and Shepherd, R. J. (1995) Analysis of the figwort mosaic virus (FMV) full-length transcript (FLt) promoter: Developing and testing of plant expression vectors with the FMV FLt promoter containing single or duble enhancer domains. In: Proceedings of the International Symposium on Engineering Plants for Commercial Products and Applications. Oct. 1–4, 1995, University of Kentucky, Lexington, Ky., USA. (Abstract # 28)

Maiti, I. B., S. Gowda, S., Kiernan, J., Ghosh, S. K., and Shepherd, R. J. (1996) Promoter/leader deletion analysis and plant expression vectors with the figwort mosaic virus (FMV) full-length transcript (FLt) promoter containing single or double enhancer domains. Transgenic Research (in press).

Maiti, I. B. Von Lanken, C., and Hunt, A. G. 1995 Properties of transgenic plants that express a functional potyvirus P1 proteinase gene. Manuscript submitted Maiti, I. B., and Hunt, A. H. 1992. Expression of the tobacco vein mottling virus nuclesr inclusion protein (NIa) gene in tobacco. J. Cell. Biochem. Supplement 16F, Abs# Y213.

Maiti, I. B., Hunt, A. G., and Wagner, G. J. 1988. Seed-transmissible expression of mammalian metallothionein in transgenic tobacco. Biochem. Biophys. Res. Commun. 150: 640–647.

Maiti, I. B., Hong, Y., Hellman, G. M., Lanken, C. V. and Hunt, A. 1994. Multiple potyvirus genes do not confer protection upon plants additively. In 4th congress of ISPMB meeting, Jun. 19–24, 1994. Amsterdam, The Netherlands, (abstract).

Maiti, I. B., Murphy, J., Shaw, J. G., and Hunt, A. H. (1991) Expression of the tobacco vein mottling virus coat protein (CP) and cylinderical inclusion protein (CI) genes in tobacco. In 3rd Int. Congress Int. Soc. Plant Mol. Biol. p1154.

Maiti, I. B., Murphy, J. F., Shaw, J. G., and Hunt, A. G. (1993) Plants that express a potyvirus Vpg-proteinase gene are resistance to virus infection. Proc. Natl. Acad. Sci. (USA) 90: 6110–6114.

Maiti, I. B., Wagner, G. J. and Hunt A. G. (1991) Light inducible and tissue-specific expression of a chimeric mouse metallothionein cDNA gene in tobacco. Plant Science 76: 99–107.

Maiti, I. B., Wagner, G. J., Yeargan, R., and Hunt, A. G. (1989) Inheritance and expression of the mouse metallothionein gene in tobacco. Plant Physiol. 91: 1021–1024.

Maiti, I. B. and Hunt, A. G. (1992) Developing genetically engineered disease, pest and herbicide resistance in tobacco. Rec. Adv. Tobacco Sci. 18: 45–68.

McNeall, J., Sandey, A. Gray, P. P. Chesterman, C. N. and Sleigh, M. J. 1989. Hyperinducible gene expression from a metallothionein promoter containing addetional metal responsive elements. Gene 76: 81–88. Odell, J. T., Nagy, F. and Chua, N-H. (1985) Identification of DNA sequence required for activity of the cauliflower mosaic virus 35S promoter. Nature 313: 810–812.

Odell, J. T. and Howell, S. H. (1980) The identification, mapping and characterization of mRNA for p66, a cauliflower mosaic virus-encoded protein. Virology 102: 349–359.

Odell, J. T., Dudley, R. K. and Howell, S. H. (1981) Structure of the 19S RNA transcripts encoded by the cauliflower mosaic virus genome. Virology 111: 377–385.

Odell, J. T., Knowlton, S., Lin, W, and Mauvais, C. J. (1988) Properties of an isolated transcription stimulating sequence derived from the cauliflower mosaic virus 35S promoter. Plant Mol. Biol. 10: 263–272.

Omirulleh, S., Abraham, M., Golovkin, M., Stefanov, I., Karabaev, M. K., Mustardy, L., Morocz, S. and Dudits, D. (1993) Activity of a chimeric promoter with the double CaMV 35S enhancer elements in protoplast-derived cells and transgenic plants in maize. Plant Mol. Biol. 21: 415–428.

Ondek, B., Gloss, L. and Herr, W. (1988) The SV 40 enhancer contains two distinct levels of organization. Nature 333, 40–45.

Ow, D. W., Jacobs, J. D. and Howell, S. H. (1987) Functional region of the cauliflower mosaic virus 35S RNA promoter determined by the use of the firefly luciferase gene as a reporter of promoter activity. Proc. Natl. Acad. Sci. USA 84: 4870–4874.

Prat, S., Willmitzer, L. and Sanchez-Serrano, J. J. 1989. Nuclear protein binding to a cauliflower mosaic virus 35S truncated promoter. Mol. Gen. Genet. 217: 209–214.

Reddy, D. V. R., Richins, R. D., Rajeshwari, R., Iizuka, N., Manohar, S. K. and Shepherd, R. J. (1993) Peanut chlorotic streak virus, a new caulimovirus infecting peanuts (*Arachis hypogaea*) in India. Phytopathology 83: 119–133.

Richins, R. D. (1993) Organization and expression of the peanut chlorotic streak virus genome. Ph. D. Dissertation, at the University of Kentucky, Lexington, Ky., USA.

Richins, R. D., Broos, T., Ducasse, D. A., Gowda, S., Mushegian, A. R., Reddy, D. V. R. and Shepherd, R. J. (1995) Organization and transcription of the peanut chlorotic streak virus genome. Mol. Plant Microbe Interact. (in press).

Richins, R. D., Scholthof, H. B. and Shepherd, R. J. (1987) Sequence of figwort mosaic virus DNA (caulimovirus group). Nucleic Acids Res. 15: 8451–8466.

Sanger, M., Daubert, S. and Goodman, R. M. (1990) Characteristics of a strong promoter from figwort mosaic virus: comparision with the analogous 35S promoter from cauliflower mosaic virus and the regulated mannopine synthase promoter. Plant Mol. Biol. 14: 433–443.

Schardl, C. L., Byrd, A. D., Benzion, G., Altschuler, M. A., Hildebrand, D. F. and Hunt, A. G. (1987) Design and construction of a versatile system for the expression of foreign genes in plants. Gene 61: 1–11.

Schirm, S., Jiricny, J. and Schaffner, W. (1987) The SV40 enhancer can be dissected into multiple segments, each with a different cell type specificity. Genes. Dev. 1: 65–74.

Scholthof, H. B., Gowda, S., Wu, F. and Shepherd, R. J. (1992) The full-length transcript of a caulimovirus is a polycistronic mRNA whose genes are transactivated by the product of gene VI. J. Virol. 66: 3131–3139.

Shepherd, R. J., Richins, R. D., Duffus, J. E. and Handley, M. K. (1987) Figwort mosaic virus: properties of the virus and its adaption to a new host. Phytopathology 77: 1668–1673.

Shepherd, R. J. (1989) Biochemistry of DNA plant viruses. In: "The Biochemistry of Plants" (A. Marcus, ed.), pp563–661, Academic Press, Inc., New York.

Takatsui, H., Yamauchi, H., Watanabe, S., Kato, H., and Ikeda, J-E. (1992) Cauliflower mosaic virus reverse transcriptase: Activation by proteolytic processing and functional alteration by terminal deletion. J. Biol. Chem. 267: 11579–11585.

Thomas, C. L., Perbal, C., and Maule, A. J. (1993) A mutation in cauliflower mosaic virus gene I interferes with virus movement but not virus replication. Virology 192: 415–421.

Thomson, D., and Henry, R. (1993) Use of DNA from dry leaves for PCR and RAPD analysis. Plant Mol. Biol. Rep. 11: 202–206.

Wagner, G. J. 1992. Improving tobacco through metabolic engineering: Promise and obstacles. Rec, Adv. Tobacco. Sci. 18: 3–43.

Woolston, C. J., Covey, S. N., Penswick, J. R. and Davies, J. W. (1983) Aphid transmission and polypeptide are specified by a defined region of the cauliflower virus genome. Gene 23: 15–21.

Wurch, T., Guidasci, T, Geildreich, A., Lebeurier, G., and Mesnard, J-M. (1991) The cauliflower mosaic virus ORF VII product can be expressed in yeast but is not detected in infected plants. J. Virol. 64: 2594–2598.

Yanagisawa, S. and Izui, K. 1992. MNF1, a leaf tissue-specific DNA-binding protein of maize, interacts with the cauliflower mosaic virus 35S promoter as well as the C4 photosynthetic phosphoenolpyruvate carboxylase gene promoter. Plant mol. Biol. 19: 545–553.

Yeargan, R., Maiti, I. B., Nielsen, M. T., Hunt, A. G., and Wagner, G. J. 1992. Tissue partitioning of cadmium in transgenic tobacco seedlings and field grown plants expressing the mouse metallothionein I gene. Transgenic Research 1: 261–267.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 352 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| ACAGAGGGAT | TTCTCTGAAG | ATCATGTTTG | CCAGCTATGC | GAACAATCAT | CGGGAGATCT | 60 |
| TGAGCCAATC | AAAGAGGAGT | GATGTAGACC | TAAAGCAATA | ATGGAGCCAT | GACGTAAGGG | 120 |
| CTTACGCCAT | TACGAAATAA | TTAAAGGCTG | ATGTGACCTG | TCGGTCTCTC | AGAACCTTTA | 180 |
| CTTTTTATAT | TTGGCGTGTA | TTTTTAAATT | TCCACGGCAA | TGACGATGTG | ACCTGTGCAT | 240 |
| CCGCTTTGCC | TATAAATAAG | TTTAGTTTG | TATTGATCGA | CACGATCGAG | AAGACACGGC | 300 |
| CATTTGGACG | ATCATTTGAG | AGTCTAAAAG | AACGAGTCTT | GTAATATGTT | TT | 352 |

( 2 ) INFORMATION FOR SEQ ID NO:2:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | | |
|---|---|---|---|---|---|---|
| GAGATCTTGA | GCCAATCAAA | GAGGAGTGAT | GTAGACCTAA | AGCAATAATG | GAGCCATGAC | 60 |
| GTAAGGGCTT | ACGCCATTAC | GAAATAATTA | AAGGCTGATG | TGACCTGTCG | GTCTCTCAGA | 120 |
| ACCTTTACTT | TTTATATTTG | GCGTGTATTT | | | | 150 |

( 2 ) INFORMATION FOR SEQ ID NO:3:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| | | | | | | |
|---|---|---|---|---|---|---|
| GAGATCTTGA | GCCAATCAAA | GAGGAGTGAT | GTAGACCTAA | AGCAATAATG | GAGCCATGAC | 60 |
| GTAAGGGCTT | ACGCCATT | | | | | 78 |

We claim:

1. A DNA construct comprising a full-length transcript promoter from peanut chlorotic streak virus, at least one enhancer domain from peanut chlorotic streak virus, a heterologous gene and border regions from *Agrobacterium tumefaciens*, wherein said promoter is operably linked to said heterologous gene.

2. The DNA construct of claim 1, wherein said at least one enhancer domain is a single enhancer domain.

3. The DNA construct of claim 1, wherein said at least one enhancer domain is a double enhancer domain.

4. The DNA construct of claim 1, wherein said promoter comprises the nucleotide sequence of SEQ ID NO:1.

5. The DNA construct of claim 1, having the designation pKLP6 or pKLP36, which is transformed in *Escherichia coli* and deposited as Accession No. NRRL B-21604 or Accession No. NRRL B-21605.

6. The DNA construct of claim 1, further comprising a non-translated leader sequence from peanut chlorotic streak virus.

7. A microorganism transformed with the DNA construct of claim 1.

8. The microorganism of claim 7, which is *Escherichia coli*.

9. The microorganism of claim 8, having Accession No. NRRL B-21604 or Accession No. NRRL B-21605.

10. A plant cell transformed with the DNA construct of claim 1.

11. The plant cell of claim 10, wherein said at least one enhancer domain of said DNA construct is a double enhancer domain.

12. The plant cell of claim 10, which is a cell from a plant selected from the group consisting of cotton, soybean, alfalfa, oilseed rape, flax, tomato, sugar beet, sunflower, potato, tobacco, maize, wheat, rice, lettuce and banana.

13. The plant cell of claim 2, which is a tobacco cell.

14. The plant cell of claim 10, which is from a tissue selected from the group consisting of calyx, filament, pedicel, style, ovary, corolla, anther, stigma, leaf, seed, embryo, stem and root.

15. A plant transformed with the DNA construct of claim 1.

16. The plant of claim 15, which is selected from the group consisting of cotton, soybean, alfalfa, oilseed rape, flax, tomato, sugar beet, sunflower, potato, tobacco, maize, wheat, rice, lettuce and banana.

17. The plant of claim 16 which is tobacco.

* * * * *